(12) United States Patent
Gonzales Rengifo et al.

(10) Patent No.: US 7,985,434 B2
(45) Date of Patent: Jul. 26, 2011

(54) **COMPOSITIONS OF ATOMIZED OR LYOPHILIZED MACA (*LEPIDIUM MEYENII*) EXTRACTS AND ATOMIZED OR LYOPHILIZED YACON (*SMALLANTHUS SANCHIFOLIUS*) EXTRACTS AS ADJUVANTS IN THE TREATMENT OF DIFFERENT CONDITIONS**

(75) Inventors: Gustavo Francisco Gonzales Rengifo, Lima (PE); Carla Jeannine Gonzales Arimborgo, Lima (PE)

(73) Assignee: Universidad Peruana Cayetano Heredia (PE)

( * ) Notice: Subject to any disclaimer, the term of this patent is extended or adjusted under 35 U.S.C. 154(b) by 18 days.

(21) Appl. No.: 12/463,224

(22) Filed: May 8, 2009

(65) Prior Publication Data

US 2009/0280203 A1    Nov. 12, 2009

(51) Int. Cl.
   *A01N 65/00*    (2009.01)
(52) U.S. Cl. .......................................... 424/725
(58) Field of Classification Search .................. None
   See application file for complete search history.

(56) References Cited

U.S. PATENT DOCUMENTS

2004/0137131 A1*  7/2004  Bobrowski ..................... 426/615

FOREIGN PATENT DOCUMENTS

JP    02000319120    * 11/2000
JP    2005306768     * 11/2005

* cited by examiner

*Primary Examiner* — Michael Meller
(74) *Attorney, Agent, or Firm* — Galbreath Law Offices, P.C.; John A. Galbreath

(57) ABSTRACT

The present invention refers to compositions of atomized or lyophilized extracts of selected maca hypocotyls of the red and black variety and atomized or lyophilized parts of the yacon plant selected from leaves and roots. The invention also refers to the methods to prepare such compositions using aqueous or hydroalcoholic extraction processes. Likewise, as novel element of the maca hypocotyls extraction process is the selection of the batches of maca hypocotyls having a pH of less than 5.5, which have better biological activity than those with a greater pH. The compositions of the invention are useful in the treatment of different conditions and diseases.

21 Claims, 11 Drawing Sheets

FIG. 1ª  SHAM + WATER

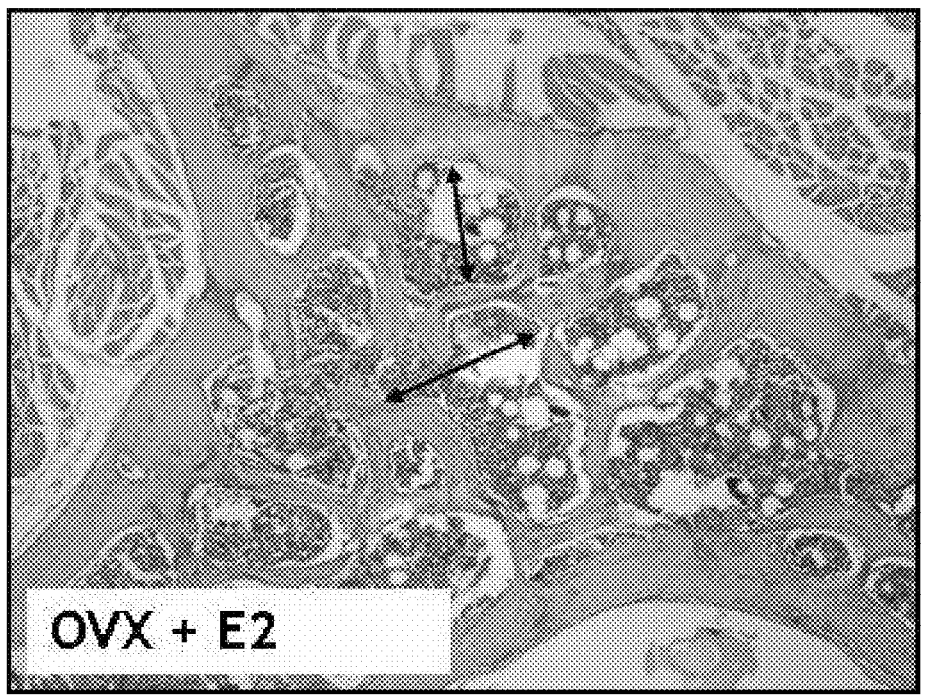
FIG. 1C
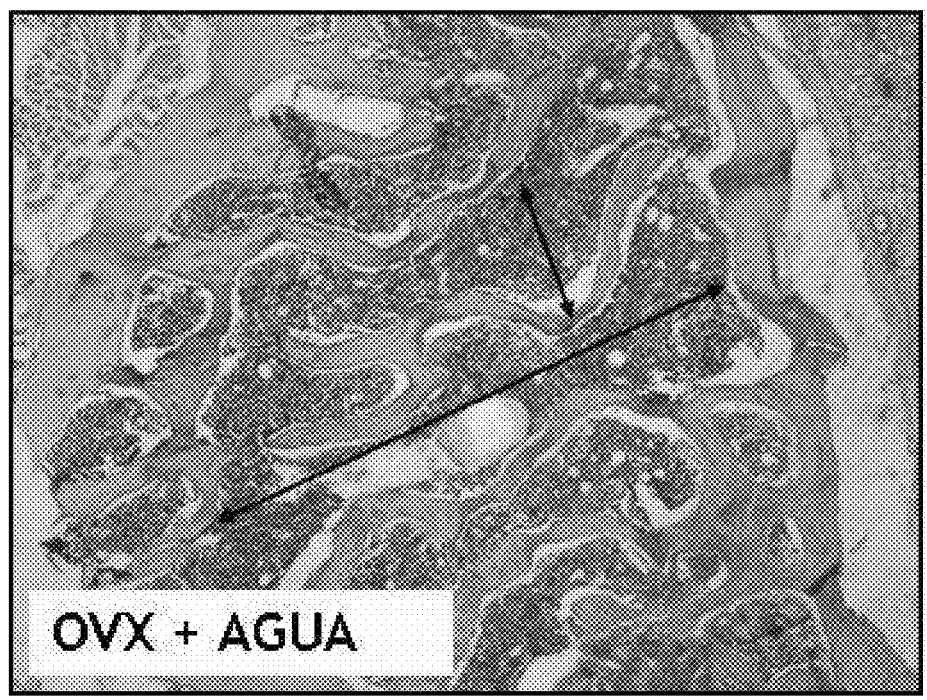
FIG. 1D  OVX + WATER

COMPOSITIONS OF ATOMIZED OR LYOPHILIZED MACA (*LEPIDIUM MEYENII*) EXTRACTS AND ATOMIZED OR LYOPHILIZED YACON (*SMALLANTHUS SANCHIFOLIUS*) EXTRACTS AS ADJUVANTS IN THE TREATMENT OF DIFFERENT CONDITIONS The present application claims priority of the Peruvian Application No. 00809-2008/OIN filed on May 8, 2008.

FIELD OF THE INVENTION

The present invention refers to compositions of maca and yacon plants extracts, the methods to prepare them, as well as their application in the treatment of different disorders and diseases.

BACKGROUND OF THE INVENTION

Notwithstanding the great progresses in the allopathic medicine, the whole world has always shown great interest in the use of medicinal plants to treat their sicknesses and diseases.

One of the main diseases is diabetes mellitus which affects 5% of the population worldwide. Diabetes mellitus is a disorder in the metabolism of carbohydrates and lipids that has a hereditary character and that contributes to increasing the death rate due to vascular, neurological and renal disorders, among others. This pathology is also associated to infertility in both sexes as well as to erectile dysfunction in men, so its prevention is important to prevent such sequels.

Another main condition in women is post-menopause, in which the sexual and depressive symptoms are the most severe (Amore et al., 2007), observing a decline in memory (Elsabath et al., 2005) and greater fatigue. Another important condition that affects women is osteoporosis, which can lead to impairment and death.

Men are affected by the prostatic hyperplasia, an important condition. The percentage of population affected by this condition is 50% at 50 years of age, increasing to 80% towards the end of the eighth decade of life.

Given the problematic mentioned above, the existence and use of a food supplement that attacks each of the conditions mentioned above and that, thanks to its properties, resulted in an energizing, and memory and learning enhancer complement would be ideal.

Peru is characterized by a great vegetal biodiversity, combined with an ancestral culture of its use for medicinal purposes that is very deeply-rooted in the Andean and Amazonian peoples. However, this traditional medicine is mono-herbal; that is, each health problem is treated with one plant, unlike the Hindu, Chinese and Korean cultures where mixtures of several plants (poly-herbal) are frequently used to solve health problems. Another difference is that the traditional Peruvian knowledge is transmitted orally, and little or none of it is recorded in reliable texts. Ignorance of writing in the pre-Hispanic age is one of the causes of the absence of much traditional information, although part of it has been included in written documents as of the Spanish conquest, particularly through the chroniclers.

The representative varieties of Peru used in the present invention are maca (*Lepidium meyenii*) and yacon (*Smallanthus sanchifolius*), each of which has interesting therapeutic properties and which will be discussed in detail below.

MACA

Generalities

Maca (*Lepidium meyenii*) is a plant of the Brassicaceae family originating in the central Andes of Peru, characterized by its capacity to grow in areas above 4000 meters of altitude where other plants hardly grow. Maca has different varieties characterized by the external color, of which 13 varieties have been identified in the area of Carhuamayo, Junin (Peru) ranging from white to black (Tello et al., 1992). Yllescas (1994) has studied the primary components of three varieties: red, yellow and black. Differences are found regarding the content of pure protein, soluble sugars by direct reduction, riboflavin, potassium and iron (Yllescas, 1994;Gonzales, 2006).

It is presumed that the domestication process of maca began two thousand years ago in Ondores, Peru (Matos, 1975; see Gonzales, 2006a). The cultivation of maca is centered in Chincaycocha, a region located in the central Andes of Peru as described in the conquest chronicles and in subsequent reports (Cieza de León, 1553;Cobo, 1653;Ruiz, 1952). By the second half of the $20^{th}$ century, maca continued being described as exclusive of the central Andes (León, 1964).

The hypocotyls are the edible part of the plant, which comprises the bulbous part that grows under the cotyledons and is similar to a radish of approximately 8 cm diameter and that grows under the ground. In 2003, Marin-Bravo described that the maca grown in the coastal area does not develop the reserving organ that characterizes the hypocotyls obtained in the central Andes.

For its consumption, traditionally, the maca hypocotyls are first dehydrated naturally, its diameter being reduced practically to 3-4 cm, washed with warm water, then soaked in boiled water overnight and then subject to cooking during one or two hours with the same liquid it was soaked in until obtaining a dark brown liquid (Córdova, 2003). Another ancestral custom is to cook the maca in a clay pot during the night, let it settle overnight and finally consume it whole or blended with the same liquid it was boiled in (Córdova, 2003; Gonzales, 2006).

It has been scientifically shown that naturally dried and boiled maca has energizing properties, properties on memory and learning, and also therapeutic properties for osteoporosis, prostatic hyperplasia and in the improvement of fertility. The descriptions about the biological effects of black maca and red maca appear as a result of the experimental work and published as of 2005 (Gonzales et al., 2005; 2006; 2007; 2008;Rubio et al., 2007).

Extraction Processes

Chacón (1961) uses 3 alkaloidal extracts to verify the biological effect of maca on fertility. The methodological design is, however, poor and has been criticized by others (León, 1964;Zheng et al., 2000; Gasco et al., 2008) so it is difficult to take into account any association between these extracts and the biological activity.

Zheng et al. (2000) has described an extraction method of a lipid fraction containing 20 to 30% of fatty acids of *Lepidium* and 10% of macamides (U.S. Pat. No. 6,267,995; Zheng et al., 2000).

Diverse producers use the ethanolic maceration stage as described by Tello and Porras, (1999) or in U.S. Pat. No. 6,267,995.

In the inventors' laboratory, the effect of a synthetic macamide, N-benzyl-5-oxo-6E, 8E-octadecadienamide, has been tested, which had no effect in the count or daily production of spermatozoids (Gonzales, 2006 page 104). Recently in the inventors' laboratory, it has not been observed either that another macamide, N-benzyl-hexadecanamide, has an effect on the number of spermatozoids in mice unlike the atomized hydroalcoholic extract of black maca that significantly increases it. Most of the biological activity is rather found in the more polar fractions (Gonzales, 2006; 2006a; Valerio & Gonzales, 2005).

Zolezzi (1997) mentions that dried and washed maca can be macerated in alcohol. The maceration can be done by introducing 20 g to 40 g of maca per liter of alcohol and letting macerate for at least five days. However, due to the characteristics of maca, this is not advisable, since the proteins, minerals, as well as some carbohydrates are not soluble in such an extract and they would be lost, unless the remaining filtrate is dried and reused. This process will extract the alkaloids, as well as some soluble glycosides. The biological activity of this preparation is not mentioned.

Garró et al., 1993 has achieved separating four alkaloid fractions from dry and pulverized hypocotyls of the plant; however, the alkaloids responsible for the biological effects of the maca have not been identified. It is necessary to specify that maca may have antagonist effects, for example, black maca increases the mitosis or is anti-apophtotic and increases the production of spermatozoids (Gonzales et al., 2006) while red maca decreases the mitosis or is apophtotic (Gonzales et al., 2005).

Chacón (1961) in his Bachelor thesis "Phytochemical Study of *Lepidium meyenii* Walp" indicates the process of extraction of secondary metabolites from 50 g of the pulverized maca product corresponding to hypocotyls grated and desiccated in the stove at 70° C.-75° C. during 12 hours, which is subjected through a soxhlet to the successive action of the solvents such as acetone, ether, alcohol and distilled water. The tests are carried out at the boiling temperature of the solvent. Chacón (1961) concludes that he has found three alkaloids, starch, glucides, fatty acids, tanines and scarce concentration of saponines. In the conclusions he mentions that the preliminary observations of the administration of the alkaloidal extract of *Lepidium meyenii* to rats and toads shows the following effects: a) Increase in the procreation of albino rats; b) Clear and marked stimulation of the follicular maturation also in albino rats; c) No effect on the spermatogenesis induced in the toad. The design of Chacón (1961) has been objected by other researchers (León, 1964, Zheng et al., 2000; Ruiz-Luna et al., 2005; Gasco et al., 2008) due to the small number of animals employed (in most cases it refers only to one animal), the time of administration, since the biological markers were subjective more than quantitative, and finally it does not use statistical analyses. Moreover, the effects over the spermatogenesis have been clearly established in studies in the inventors' laboratory (Gasco et al., 2007;Gonzales 2006; 2006a; Rubio et al., 2006a).

Regarding the extraction with water, no specification exists about the optimum water volume and the time of cooking (Gonzales et al., 2006a; Córdova, 2003). Cóndor (1991) prepares extracts base on 100 g of maca in 300 ml of water and finds out that the treatment reduces the number of empty or aborted ewe hoggs. Zolessi (1997) describes maca is boiled in the same amount of water during thirty to sixty minutes. Then it can be blended with the cooking water adding other ingredients or the maca can simply be consumed separately and the cooking water as a beverage. He does not say if this preparation has any verifiable biological activity.

Maca Products

The commercial products of maca include tablets, pills, capsules, flours, liquors, tonics and mayonnaise (Li et al., 2001), which are mostly constituted by maca flour with or without gelatinization. In the case of tablets or capsules, these contain between 450 and 500 mg of maca hypocotyls and the amount prescribed of 3 to 6 tablets or capsules per day would correspond to 3 grams of hypocotyls, a value that is very far from the average daily consumption of an inhabitant of the central Andes, which is estimated in 20 to 40 grams. To consume 40 grams of hypocotyls a person would have to take more than 80 capsules or tablets per day.

In the case of maca flour, whether dry or fresh, since it has not undergone the traditional preparation process it lacks the therapeutic properties or in any case such properties are diminished. On the other hand, such maca flour has a low solubility in water, which is improved in gelatinized maca. The solubility in water is optimum if the product proceeds from aqueous or boiled hydroalcoholic extraction processes.

The maca flour has a strong flavor, very peculiar in this plant, which is not acceptable by many people not used to its use (De Rivero and Ustariz, 1897). The foregoing problem is solved by adding juices and other mixtures to disguise its flavor (Quiroz and Aliaga, 1997). Another inconvenience is that the consumption of maca flour causes digestive discomforts.

Biological Activity

Besides the well-known nutritional effects (Canales et al., 2000), on the spermatogenesis (Gonzales et al., 2001; 2001a) and fertility (Cobo, 1653;Chacón, 1961;Cóndor, 1991), the energizers, antidepressants, anxiolytics (Gonzales, 2006; 2006a), tranquilizers (Tapia et al., 2000; Gonzales 2006; 2006a) and antioxidants of maca (Sandoval et al., 2002), have demonstrated some particular properties in varieties of maca such as the black and the red maca. It has recently been demonstrated that red maca reduces the size of the prostate in the benign prostatic hyperplasia experimentally induced in rodents (Gonzales et al., 2005; 2007) and reverts the osteoporosis in ovariectomized rats (Carla Gonzales, not published, see FIG. 1). On the other hand the black maca increases the number of spermatozoids, see Table 2 in a quantity greater than with other varieties of maca such as the yellow or red maca (Gonzales C. et al., 2006), and has an effect on the improvement of memory and learning in the model of ovariectomized animals, which simulates what occurs in post-menopause women (Rubio et al., 2006), or in the model of animals treated with scopolamine, which experimentally simulates the Alzheimer Disease (Rubio et al., 2007). The black and red varieties of maca have an important antioxidant activity, which represents a potential food supplement advisable for people's health (Gonzales, not published).

Secondary Metabolites

In many cases it has been intended to associate the presence of secondary metabolites such as macaenos and macamides (Zheng et al., 2000), prostaglandins, sterols, and amides of poly-unsaturated fatty acids in the hypocotyls-root (Li et al., 2001) of maca with its biological properties. Thus, the properties of maca to improve fertility have suggested that they could be due to the presence of biologically active isothiocyanates derived from the hydrolysis of glucosinolates specifically due to the benzyl-isothiocyanate and the p-methoxybenzyl isothiocyanate (Johns, 1981;Li et al., 2001). However, there is no study wherein a specific compound of maca is isolated and that administered to experimental animals has demonstrated any biological effect, reason why any statement of the biological properties of such or such compound falls on the speculation ground. Moreover, the metabolites of the glucosinolates have pro-apophtotic and anti-proliferative properties, an effect completely opposed to the required one to increase fertility (Valreio & Gonzales, 2005).

The glucosinolates measurement is currently used to standardize the maca products. Since glucosinolates are metabolized both in the plant and in the gastrointestinal tract into isothiocyanates and these in turn into other metabolites in the organism (Gonzales & Valerio, 2006; Fahey et al., 2001), not being stable compounds they would not be adequate chemical markers. This has been demonstrated in the inventors' laboratory, where different batches with red maca with the same amount of glucosinolates for each batch show different biological responses (Gonzales, not published).

Yacon

Generalities

Yacon (*Smallanthus sanchifolius*) is an asteraceae from the Andean areas that grows in zone of not more than 3,000 meters of altitude and the culture of which has expanded to other latitudes. In Peru it is found especially in humid temperate areas in Andean slopes, in dry inter-Andean valleys, as well as in the coast. Both the tubercle and the leaves have hypoglycemic properties, properties of improvement of the lipid profile as well as of intestinal absorption of calcium. The tuberous roots of yacon accumulate almost 10%, based on the fresh weight, of inulin type fructooligosaccharides (FOSs), which are known as food ingredients with health benefits (Narai-Kanayama et al., 2007), the main saccharide being beta-1,2-oligofructane (Valentova et al., 2004). The potential of the yacon root to treat hyperglycemia, see tables 3 and 4, renal problems and for skin rejuvenation seem to be due to the oligofructanes, while the antioxidant, anti-hyperglicemic and cytoprotecting activities of the yacon leaves seem to be due to the content of phenols (Valentova and Ulrichova, 2003; Simonovska et al., 2003). The yacon root is also known for its prebiotic capacity (Pedreschi et al., 2003). Another property of yacon is that of oxygenation of the bisphenol A (Yoshida et al., 2002), and endocrine disrupter that is present in plastics, thus producing a decrease or inhibition of its noxious action to the organism.

Low temperature, high humidity storage of yacon is recommended; even so, there is a transformation of the FOSs into fructose (Narai-Kanayama et al., 2007). The tuberous roots of yacon contain phenolic, flavonoid, alkaloid, steroid, glycosides, carbohydrates compounds (Alvarez et al., 2008) and diterpenoids (Dou et al., 2008). It is possible to find the inulin in 7.8% of hydrolyzed extracts and 7.01% in non-hydrolyzed extracts (Alvarez et al., 2008).

Biological Activity

The phenolic acids of yacon seem to be responsible for its effect on the metabolism of glucose. It has been demonstrated that the caffeic, chlorogenic, rosmarinic and ferulic acids reduce the production of glucose acting over the gluconeogenesis and glucogenolysis. It has recently been demonstrated in the asteraceae, from which yacon comes from, that the phenolic compounds and the antioxidant activity increase as the growing altitude increases (Spitaler et al., 2008).

Most of the phenolic compounds studied increase the levels of the glucokinase RNAm similar to how insulin does (Valentova et al., 2007). Five derivatives of the caffeic acid have been detected in the aqueous extract of the yacon root (Takenaka et al., 2003), which may be responsible for the properties observed in this plant. The yacon roots also show an important effect by producing a positive balance of calcium and magnesium, and thus obtaining a greater osseous mineral retention (Lobo et al., 2007). The sub-chronic use for 4 months of yacon root flour in male rats was well tolerated and did not show adverse effects or toxicity at a dose of 340 mg and 6800 mg FOS/bodily weight. Under these conditions the triglyceride levels decrease although no effects were observed over the glycemia (Genta et al., 2005). The hypoglycemic effect of yacon is not due to a lower intestinal absorption of glucose (Matsuura et al., 2004). The yacon root also has antioxidant properties and among the antioxidants are the chlorogenic acid and the tryptophano (Yan et al., 1999).

The leaves have also shown having a favorable effect on the reduction of the blood glucose levels.

Extraction Processes and Biological Activity

Trying to look for better methods to extract the polysaccharides in the yacon leaves, the effect of the extraction with microwaves and with the traditional extraction with boiling water has been proven. A better extraction has been found by using microwaves at a rate of 280 W twice during 15 minutes each time (Li et al., 2007). Sesquiterpenes lactones have been found in the leaves, which inhibit the production of nitric acid induced by lipopolysaccharides (LPS) in murine RAW 264.7 macrophage cells (Hong et al., 2008). These sesquiterpene lactones have also shown antibacterial activity (Lin et al., 2003). Fluctuanine has the greatest antibacterial activity against *Bacillus subtilis* between six sesquiterpene-lactoses tested (Lin et al., 2003). The boiled aqueous extract of yacon leaves also shows an antioxidant effect of free radicals and an inhibitory activity over the lipid peroxidation in homogenized rat brain (Tereda et al., 2006). Two organic fractions and two fractions of aqueous extracts of yacon leaves show a high protective effect against the oxidative damage to primary cultures of rat hepatocytes, and a reduced hepatic production of glucose through gluconeogenesis and glucogenolisis (Valentova et al., 2004). The total content of phenols in the extracts range from 10.7 to 24.6% (Valentova et al., 2005). Two fractions of yacon leaves extracts with high content of polyphenols have a high antioxidant power (Valentova et al., 2003).

A 10% decoction of yacon produces a significant reduction of the glucose levels in normal rat plasma when the administration is intraperitoneal or in the digestive tract. Similarly, an administration of 10% of the yacon decoction produces a decrease in the levels of glucose during an oral tolerance to glucose. On the other hand, no effect was observed in diabetic rats induced by streptozotocine after the administration of the 10% yacon decoction. However, the administration of 2% yacon tea ad libitum instead of water for 30 days produced a significant hypoglycemic effect in diabetic rats induced by streptozotocine. After 30 days of administration of the tea, the diabetic rats showed improvements in the plasmatic glucose and insulin, in the bodily weight, and in renal parameters such as kidney weight/bodily weight, depuration of creatinine, urinary excretion of albumin, as compared to control diabetic rats (Aybar et al., 2001).

SUMMARY OF THE INVENTION

The present invention consists in processes to prepare compositions of maca extracts and yacon extracts. The resulting compositions comprise 3 grams of atomized or lyophilized maca hypocotyls extract, whether red or black as well as 1 gram of atomized or lyophilized yacon root or leaf extract.

Likewise, the preparation process of the maca hypocotyls extracts comprises the novel step of selecting those maca hypocotyls with a pH of less than 5.5.

One of the objectives of the invention is to prepare compositions that contain atomized or lyophilized products coming from the aqueous extraction or hydroalcoholic extraction of maca hypocotyls, whether of red or black maca, which have a concentration of maca a lot larger than the concentration of maca available in the food supplements currently in the market, likewise, such compositions contain lyophilized or atomized yacon root or leaf extracts.

Another objective of the invention is to provide the compositions that comprise the atomized or lyophilized extracts of maca and yacon conveniently placed in the form of sachets for their administration as food supplements and adjuvants in different conditions. Such extract compositions proposed in the present invention do not exist in the Peruvian or in the international market because they are novel.

Another objective of the present invention is to provide a composition of atomized or lyophilized extracts of maca and yacon, in which the problem of the strong flavor of maca and the digestive discomforts caused by the same are eliminated, and therefore a food supplement is obtained that is easily accepted by the population in need of the same.

The compositions of the present invention use as the active principle the boiled aqueous extract or the boiled hydroalcoholic extract of the maca hypocotyls.

It is another objective of the invention to provide a composition that contains red maca aqueous or hydroalcoholic extract mixed with yacon leaves or roots extracts, which is useful in the treatment of osteoporosis.

Another objective of the invention is to provide a composition that contains aqueous or hydroalcoholic extract of black maca mixed with yacon leaves or roots extract, which is useful to reduce embryonic losses.

Another objective of the present invention is to provide compositions in which, added to the effects of the maca (*Lepidium meyenii*) are the glycemia, lipid profile, calcium absorption enhancer and large intestine function regulating effects of the yacon (*Smallanthus sanchifolius*).

Still another objective of the invention is to take advantage of the property of improving the intestinal absorption of calcium of the yacon (*Smallanthus sanchifolius*) and of the property to revert the osteoporosis of the red maca (*Lepidium meyenii*), see FIGS. 1A-D as an alternative treatment, both preventive and repairing, of post-menopause events.

BRIEF DESCRIPTION OF THE DRAWINGS

FIGS. 1A-D show the effect of red maca over the osseous trabecule in ovariectomized rats. FIG. 1A shows the osseous trabecule of rats with simulated surgery and treated with the water vehicle. FIG. 1B shows the osseous trabecule of ovariectomized rats treated with red maca. FIG. 1C shows the osseous trabecule of ovariectomized rats treated with estradiol. FIG. 1D shows the osseous trabecule of ovariectomized rats treated with the water vehicle. Red maca reverts the effect of the ovariectomy. The arrows show the loss of the osseous trabecule; this is greater in FIG. 1D and less in FIG. 1B and in FIG. 1C. FIG. 1B and FIG. 1C are similar to the normal animals shown in FIG. 1A.

DETAILED DESCRIPTION OF THE INVENTION

The present invention consists in the compositions that comprise the atomized and lyophilized products of aqueous or hydroalcoholic extracts of the hypocotyls of *Lepidium meyenii* (maca), both its black and red varieties, and the atomized and lyophilized products of the extracts of *Smallanthus sanchifolius* (yacon) roots and leaves. Such compositions of maca and yacon extracts are conveniently place in sachets, and therefore the physical and therapeutic properties of such compositions remain unaltered from their manufacture to their final consumption.

Although the boiling process used in the extraction processes frequently reduces the biological activity of the active principles (Stinztzing et al., 2006), in the last few years it has been demonstrated that heating can improve the production of active principles, particularly of polyphenols (Shen et al., 2007) or derivatives of the glucosinolates, the sulphorophane with high anti-carcinogenic property (Matusheski et al., 2004). These secondary metabolites are abundant in the maca hypocotyls. In the inventors' laboratory, it has been demonstrated that the boiling process, both in water and in hydroalcoholic solution, at 50 or 70%, increases the recovery of active metabolites, the polyphenol content and the antioxidant activity in the DPPH test (Gonzales et al., not published), see Table 1.These activities are increased even more if the maca is pre-toasted for 5 minutes. The heating process is important to liberate the active principles of the plant, since the hypocotyls is constituted by a solid mass the active principle recovery of which is low if there is no boiling (Gonzales et al., not published).

Figure 11:
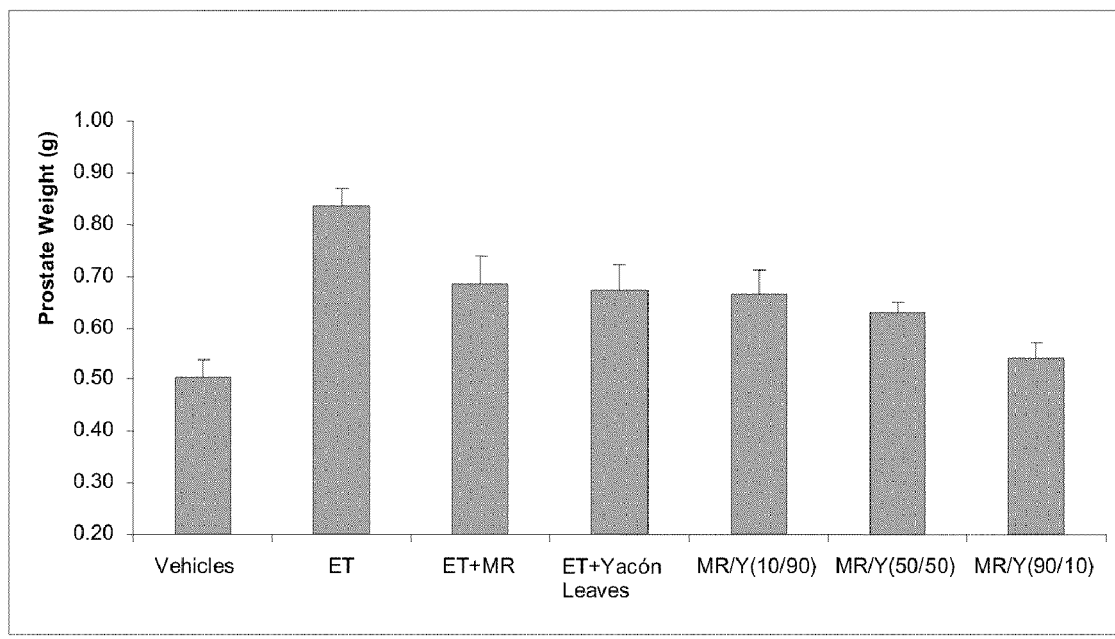
FIG. 11 shows the effect of the compositions of the extracts of the present invention on the size of prostates in rats in which prostatic hyperplasia has been induced with testosterone enantate.

The compositions comprising the atomized and lyophilized products of red maca hypocotyls extracts of the invention are useful in the treatment of the benign prostate hyperplasia. The previous statement is confirmed by the data in Table 5, which shows the weight decrease in the rodent prostates hypertrophied with testosterone enantate, by providing different compositions of boiled aqueous extracts of red maca with yacon extracts; in addition, such compositions have the advantage of reducing the levels of glucose in blood. FIG. 11 shows that both the red maca extract and the yacon leaf extract reduce the weight of the prostate in rats in which the prostatic hyperplasia has been induced with testosterone enantate. The combination of red maca+yacon leaf showed a greater reduction of the prostate weight with the advantage that the glucose levels in blood are normalized by effect of the yacon leaf, see Table 5.It had not been described until now that the yacon leaf extract had an effect on the weight of the prostate.

The yacon extracts of the present invention can add or favorably complement the effect of the maca. For example, the yacon favors the intestinal absorption of calcium (Lobo et al., 2007). The red maca has the property of reverting the osteoporosis in ovariectomized rats (Gonzales Carla et al., not published). The mixture of yacon with would favor that as the osseous mass increases due to the action of the red maca, the re-formed bone has a greater availability of calcium.

Table three shows the response in the glucose levels when black maca and yacon compositions are administered. The atomized black maca reduced the levels of glucose in blood after three days of treatment (P<0.001). This effect was not observed after 7 days of treatment. Combining the black maca with yacon a decrease of the glycemia is observed after three days of treatment. This effect is observed both with the yacon obtained at a commercial store and the one obtained directly from the field and processed in the laboratory. No dose-response effect was observed since the glycemia with the yacon at 0.01 g/kg had the same effect as with yacon 1 g/kg.

Likewise, it can be observed in Table 4 that after 7 days of treatment, the combination of black maca with yacon processed in the inventors' laboratory produced a decrease of the glycemia as compared to the control or to the group treated only with black maca. No dose-response effect was observed. Thus, the treatment with a low dose of yacon produces the same effect as with the highest dose (1 g/kg).

Figure 1B:
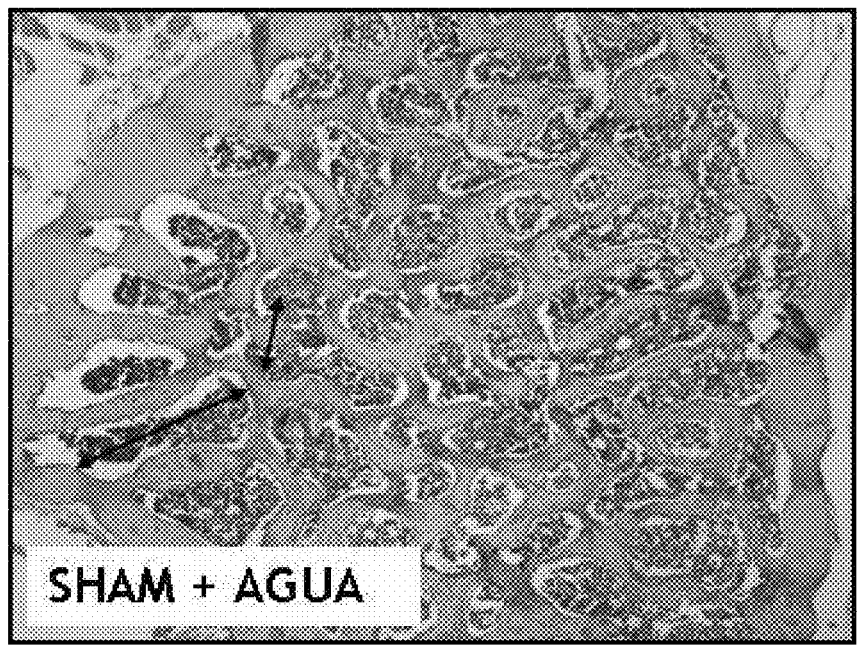
Figure 1B:
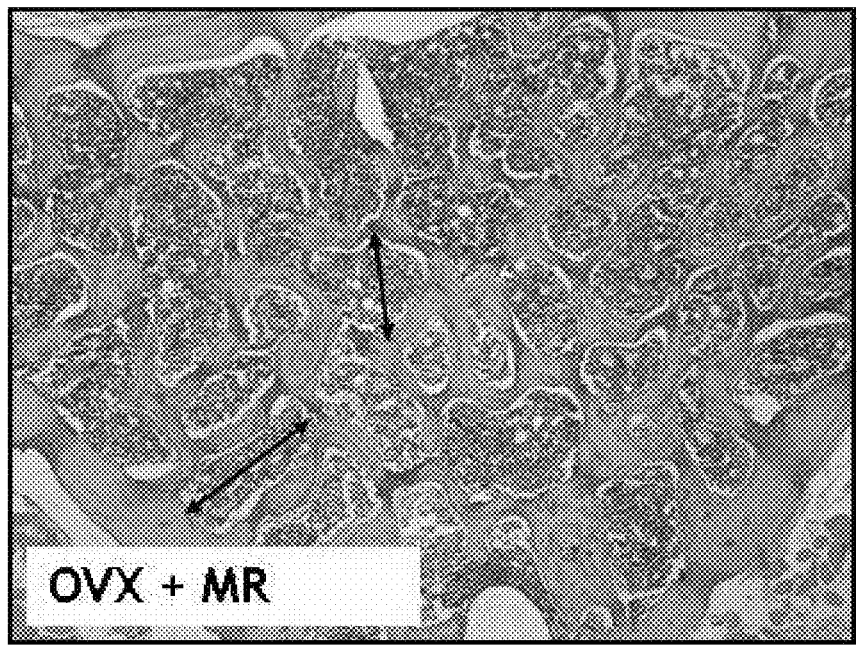
Figure 2:
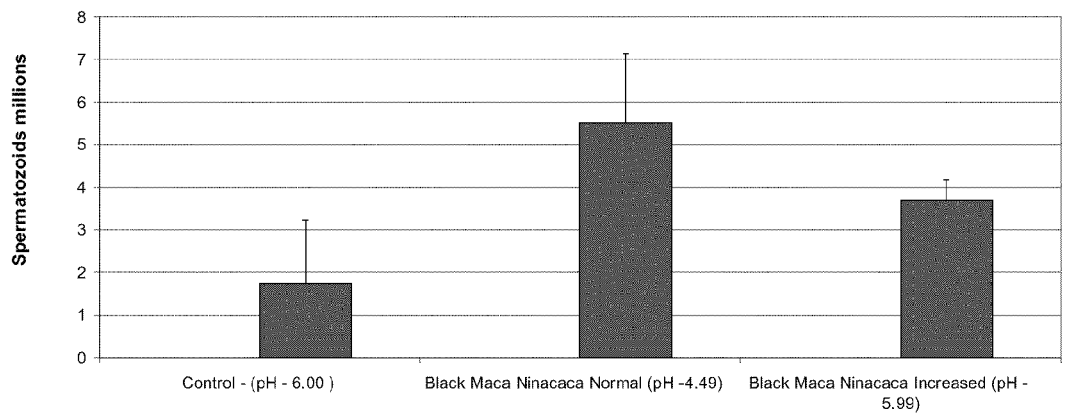
FIG. 2 shows the effect of the pH on the biological activity of the black maca of Ninacaca. If the pH is increased from 4.49 to 5.99, a reduction in the count of spermatozoids in deferent duct is observed.
Figure 3:
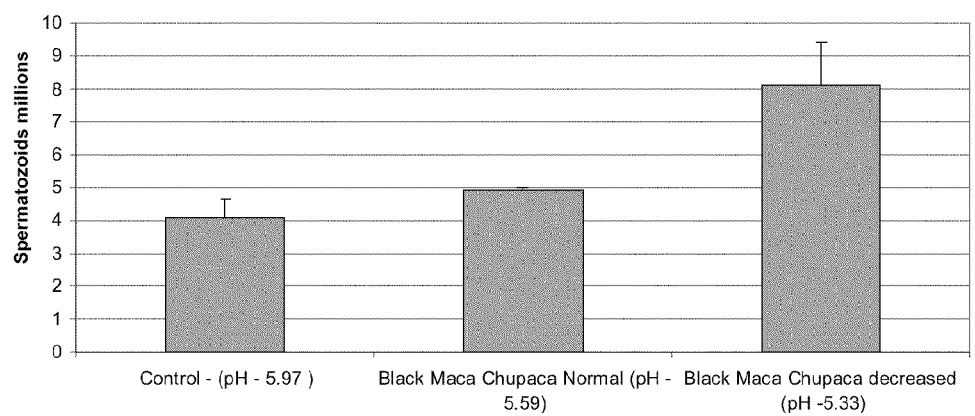
FIG. 3 shows the effect of the pH on the biological activity of the black maca of Chupaca. If the pH is reduced from 5.59 to 5.33, an increase in the spermatozoids count in deferent duct is observed.

The inventors have demonstrated that the biological activity of the maca is directly related to the pH of its hypocotyls; thus, the more acid the pH of such hypocotyls the better the biological activity of the same, see FIGS. 2 and 3, wherein it is shown that the lower the pH the higher the amount of spermatozoids in the deferent duct. Therefore, it is a novel element of the present invention the evaluation of the pH prior to processing the batches of maca hypocotyls and choosing the batches with pH$\leq$5.5 for the boiling in the aqueous or hydroalcoholic extraction processes.

The pH parameter can also serve to measure the biological quality when large batches of maca are to be purchased, whether in the cultivation field or in the dry maca storages.

The preparation process of the *Lepidium meyenii* (maca) extracts is the following:

First, batches of *Lepidium meyenii* hypocotyls are provided coming from areas located at 4000 meters of altitude, then such batches of maca hypocotyls are classified according to their color, whether red or black; they are dehydrated according to the traditional proceeding described above; they are washed, pulverized, pre-toasted for 5 minutes. Only the hypocotyls batches having a pH$\leq$5.5 are selected. Such selected batches of toasted hypocotyls can be subjected to boiling in water or, to boiling in 50 or 70% hydroalcoholic solution.

Figure 7:
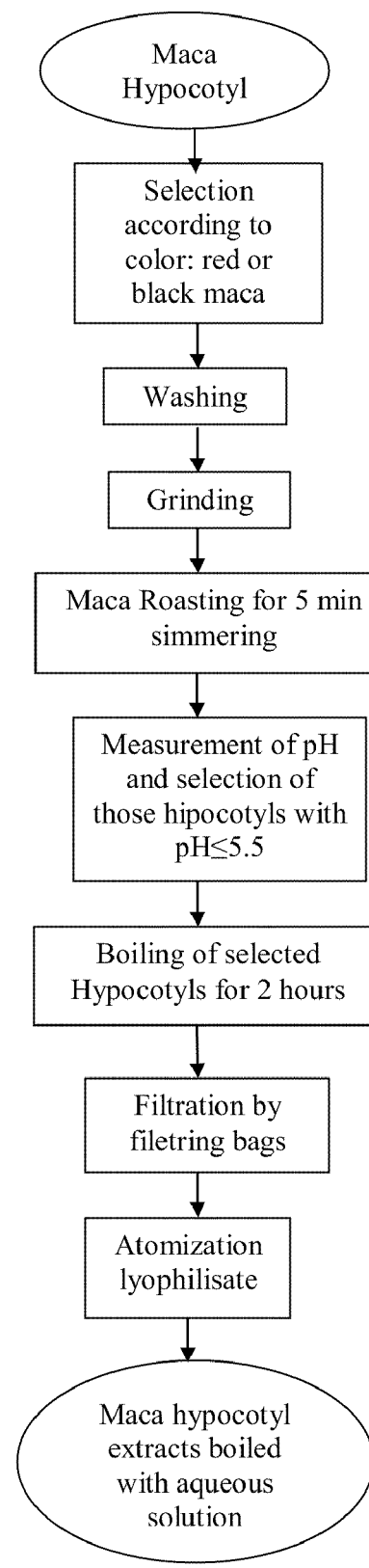
FIG. 7 shows the flow chart of the aqueous extract processing of maca.

In the case of the boiling in aqueous solution, the selected batches of toasted maca hypocotyls are boiled in water in a proportion of 1:7; 1:10 or 1:15 (weight/volume) respectively for two hours, the liquid is extracted, filtered in 80 mesh and such boiled product may be atomized or optionally lyophilized. See FIG. 7.

Figure 8:
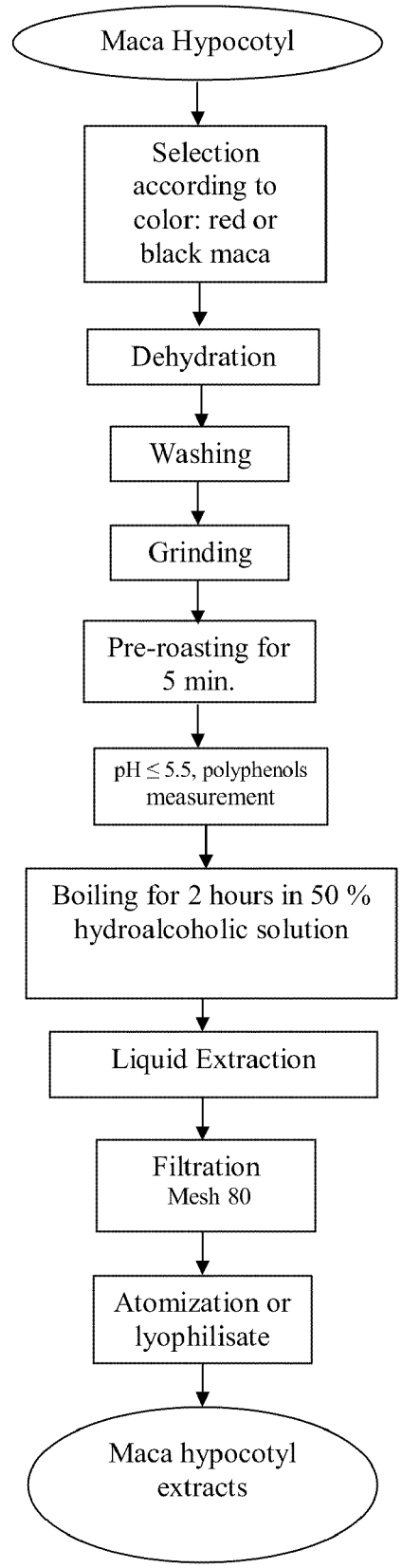
FIG. 8 shows the flow chart of the 50% hydroalcoholic extract processing of powdered maca hypocotyls.
Figure 9:
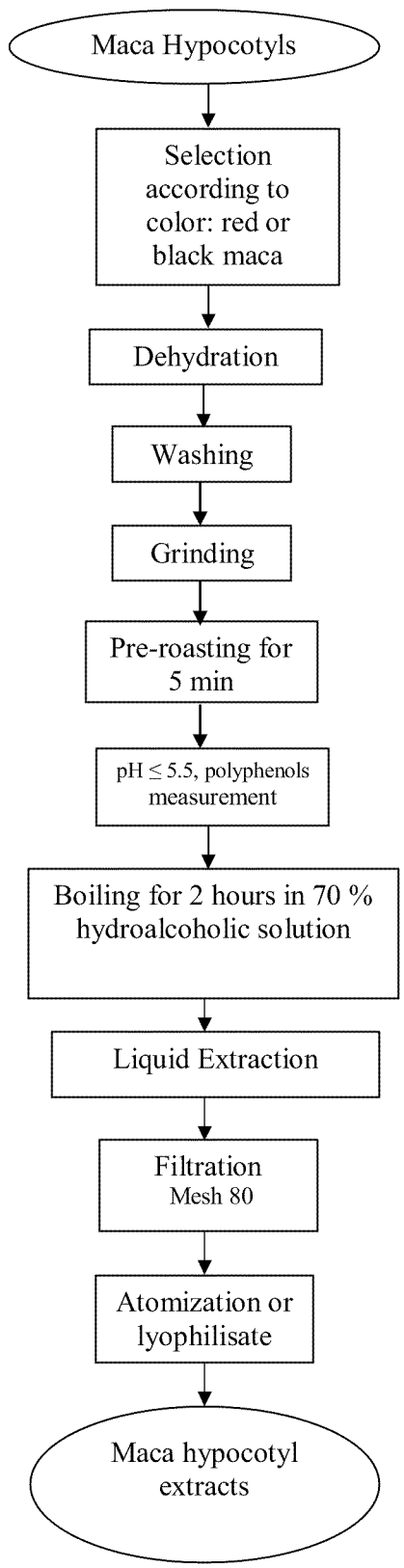
FIG. 9 shows the flow chart of the 70% hydroalcoholic extract processing of powdered maca hypocotyls.
Figure 10:
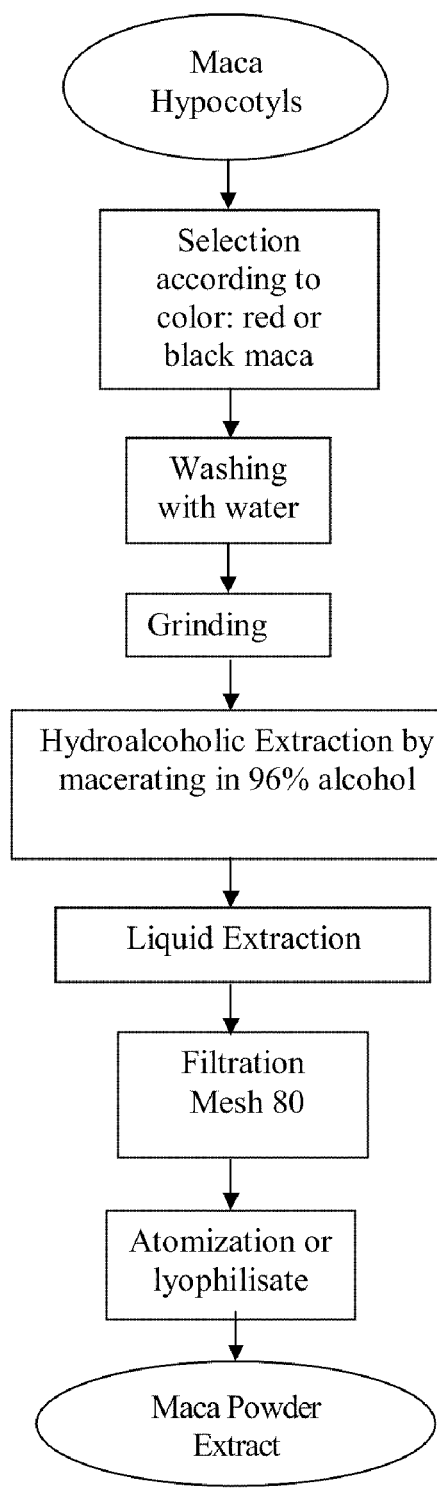
FIG. 10 shows the flow chart for the process of obtaining the macerated hydroalcoholic extract of maca hypocotyls.

In the case of the boiling in hydroalcoholic solution, the selected batches of maca hypocotyls are placed in a container with the 50 or 70% hydroalcoholic solution in a proportion of 1:7 (weight/volume) respectively and are boiled for one hour (see FIG. 8 and FIG. 9). The substances in contact are subjected to a boiling temperature of the solvent and the solutions obtained may be processed whether by atomization or by lyophilizing, both processes being conventional.

Both for the aqueous extraction and for the hydroalcoholic extraction, after maintaining contact with the aqueous or hydroalcoholic solvent, the residual material of the plant is separated and discarded.

Recently in the laboratory, the inventors have demonstrated that the aqueous or 50% or 70% hydroalcoholic extracts, previously boiled and then lyophilized or atomized have a better biological activity than the hydroalcoholic extracts macerated at room temperature which are those available in the market.

The atomized products of hydroalcoholic extracts of maca prepared for this innovation contain 11-13% proteins; 70-78% carbohydrates; 0.2-1.5% fibers, 0.2 to 0.4% lipid and 6-9% humidity. An important characteristic is their low lipid content (0.2 to 0.4%). These values differ from those reported for dry maca that contains 10.2% proteins, 59% carbohydrates, 2.2% $ lipids and 8.4% fiber (Dini et al., 1994).

The aqueous or hydroalcoholic fraction of the maca extracts contain total polyphenols ranging from 4 to 12 times the value of the pulverized maca hypocotyls. The boiled extracts have a greater content of total polyphenols than the not boiled extracts (sonicated). Pre-toasting the maca pulverized product prior to boiling it improves even more the extraction of polyphenols. The solid residue remaining after the boiling process contains a scarce amount of polyphenols as compared to the boiled aqueous extract. This process of pre-toasting prior to boiling and atomizing has not been yet described nor is it in any commercial product currently sold.

In another modality of the invention, macerated hydroalcoholic extracts of *Lepidium meyenii* can be obtained through a variant of the process. Such process comprises the following stages: batches of *Lepidium meyenii* hypocotyls coming from areas located a 4000 meters of altitude are provided, selected according to their variety, that is, red or black; such batches of *Lepidium meyenii* hypocotyls are washed and then grounded and macerated in a 50% or 70% hydroalcoholic solution for three days; then the liquid of the previous stage is extracted, filtered in 80 mesh and finally the filtered liquid portion if the previous stage is atomized or lyophilized through conventional processes.

Figure 12:
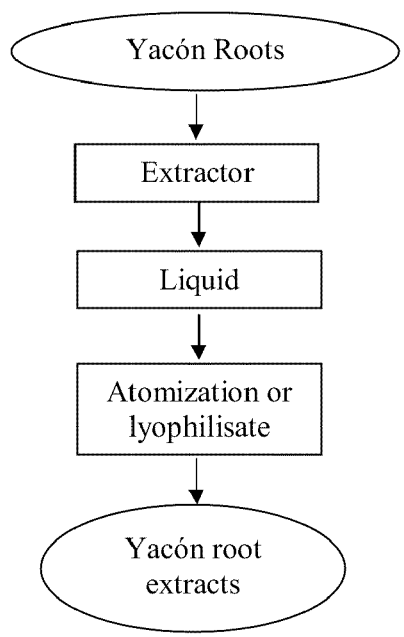
FIG. 12 shows the flow chart of the processing of yacon roots extract.
Figure 13:
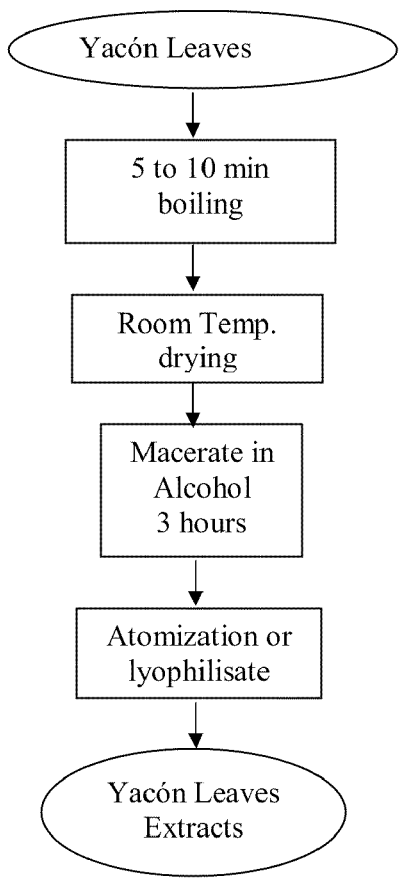
FIG. 13 shows the flow chart of the processing of yacon leaves extracts.

Regarding the manufacture of yacon extracts, the process is as follows:

(a) the yacon plant grown at an altitude of 1814 masl (in the area of Oxapampa, Peru) is selected;

(b) the parts of the yacon plant are separated and classified, whether in roots or in their corresponding leaves;

(c1) in the case of the yacon roots, these are placed in an extractor, the collected resulting liquid is measured and then atomized or lyophilized through conventional processes, see FIG. 12; or (c2) in the case of the yacon leaves, these are subjected to a boiling process for 5 to 10 minutes or; the leaves are dried at room temperature and then macerated in alcohol during three days, in a proportion of 100 grams of leaves in 1.5 liters of 96° ethanol and finally they are atomized or lyophilized through conventional processes, see FIG. 13.

The extracts resulting from the aqueous extraction, 50% or 70% hydroalcoholic extraction or, optionally, macerated in 50% or 70% hydroalcoholic solution of maca hypocotyls and of yacon leaves or roots extracts are then placed in sachets in quantities of 3 grams of atomized or lyophilized products of maca hypocotyls extracts and 1 gram of atomized or lyophilized products of yacon leaves or roots extracts, which would correspond to 20 grams of hypocotyls and 10 grams of yacon leaves or roots respectively.

The compositions of maca and yacon extracts resulting from the combination of the extracts obtained in accordance with the previous processes are the following:

Black Maca+Yacon

1. Boiled aqueous extract of black maca+aqueous extract of yacon root
2. Boiled aqueous extract of black maca+yacon leaf extract
3. Boiled 50% hydroalcoholic extract of black maca+aqueous extract of yacon root
4. Boiled 50% hydroalcoholic extract of black maca+yacon leaf extract
5. Boiled 70% hydroalcoholic extract of black maca+aqueous extract of yacon root
6. Boiled 70% hydroalcoholic extract of black maca+yacon leaf extract
7. Extract macerated in 50% hydroalcoholic solution of black maca+yacon root extract
8. Extract macerated in 50% hydroalcoholic solution of black maca+yacon leaf extract
9. Extract macerated in 70% hydroalcoholic solution of black maca+yacon root extract
10. Extract macerated in 70% hydroalcoholic solution of black maca+yacon leaf extract.

Red Maca+Yacon

11. Boiled aqueous extract of red maca+aqueous extract of yacon root
12. Boiled aqueous extract of red maca+yacon leaf extract
13. Boiled 50% hydroalcoholic extract of red maca+aqueous extract of yacon root
14. Boiled 50% hydroalcoholic extract of red maca+yacon leaf extract
15. Boiled 70% hydroalcoholic extract of red maca+aqueous extract of yacon root
16. Boiled 70% hydroalcoholic extract of red maca+yacon leaf extract
17. Extract macerated in 50% hydroalcoholic solution of red maca+yacon root extract
18. Extract macerated in 50% hydroalcoholic solution of red maca+yacon leaf extract
19. Extract macerated in 70% hydroalcoholic solution of red maca+yacon root extract
20. Extract macerated in 70% hydroalcoholic solution of red maca+yacon leaf extract.

Figure 4:
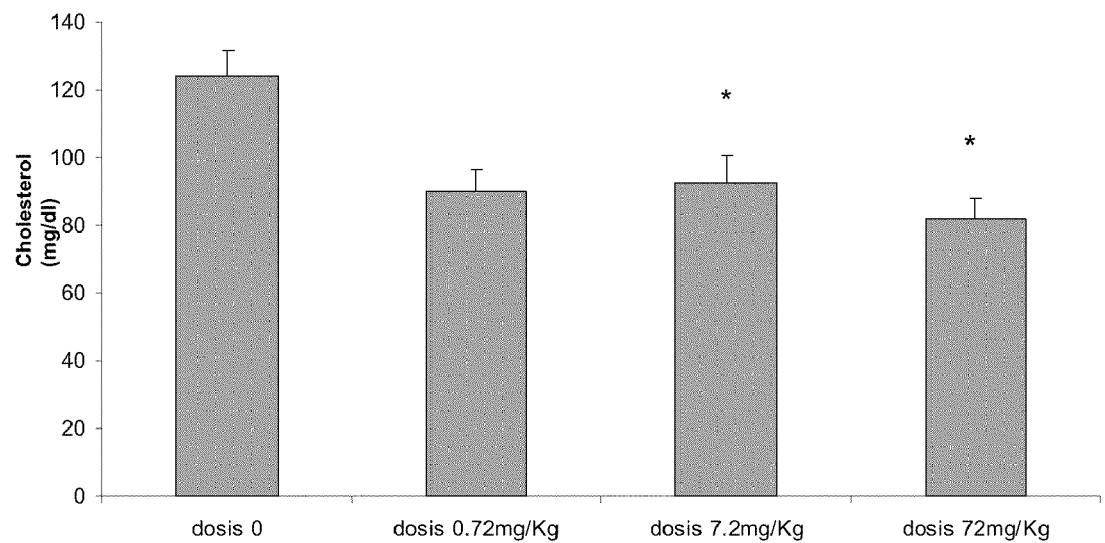
FIG. 4 shows the evaluation of total cholesterol, where there is a decrease (P<0.05) regarding the control, using boiled aqueous extract of yacon root at different doses.
Figure 5:
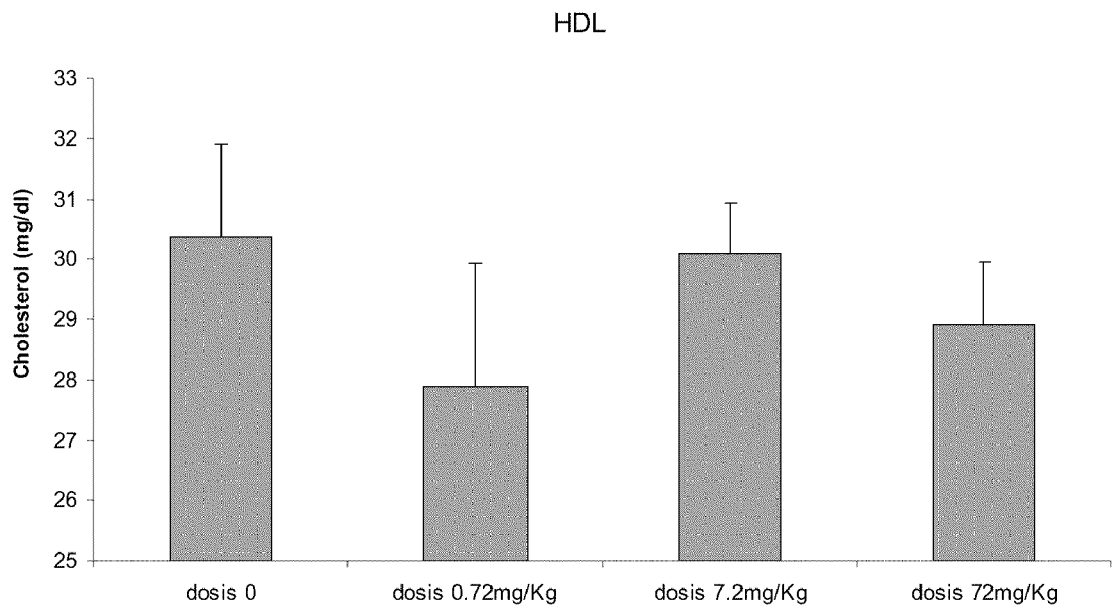
FIG. 5 shows the evaluation of HDL cholesterol, where there is no modification (P>0.05) regarding the control using boiled aqueous extract of yacon root at different doses.
Figure 6:
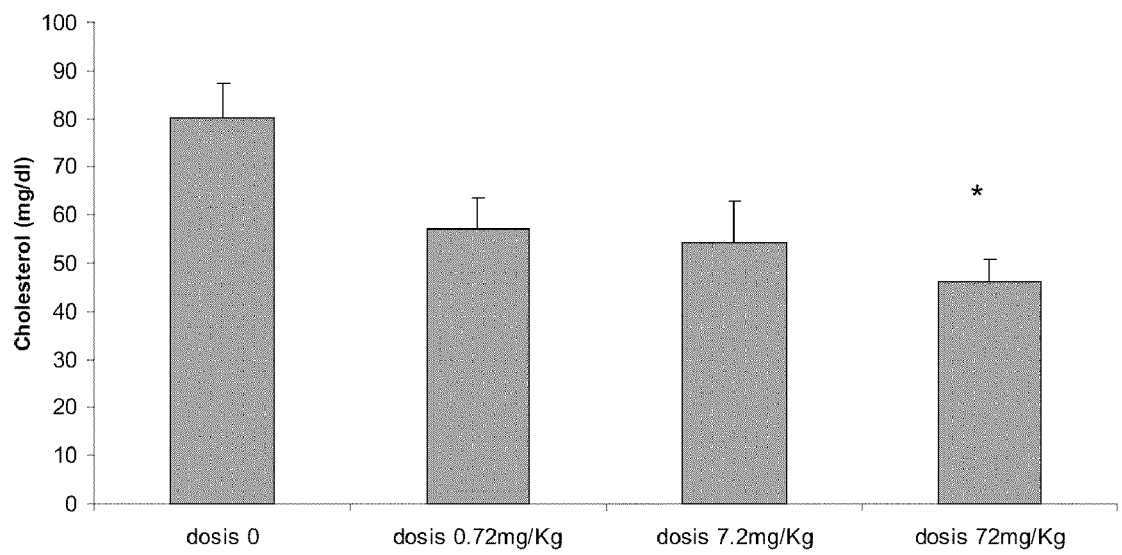
FIG. 6 shows the evaluation of LDL cholesterol, where there is a decrease (P<0.05) regarding the control using boiled aqueous extract of yacon root at different doses.

These compositions are chemically evaluated through the measurement of the content of total polyphenols, see Table 6, followed by the microbiological and nutritional evaluation and of the biological activity and finally they are stored. The mixture of maca with yacon maintains the biological activity of each of such plants (see Tables 2-4 and FIGS. 4-6).

TABLE 1

Association between levels of total polyphenols and antioxidant activity in black maca (BM). (A 0.25 mg/ml sample was used)

| Samples | Polyphenols (g/100 g) Mean (Standard error) | Antioxidant activity (%)* |
|---|---|---|
| BM in 50% boiled Ethanol | 0.45 (0.01) | 52.05 |
| BM in 70% boiled Ethanol | 0.44 (0.003) | 50.19 |
| BM in 50% sonicated Ethanol | 0.38 (0.002) | 43.97 |
| BM in 70% sonicated Ethanol | 0.36 (0.02) | 42.11 |

TABLE 2

Spermatozoid count (millions) in epididymis after three days and seven days of treatment.

| | 3 days | 7 days |
|---|---|---|
| Control | | |
| Mean ± standard error | 61.39 ± 12.40 | 83.46 ± 5.87 |
| N | 10 | 10 |
| Black maca | | |
| Mean ± standard error | 116.76 ± 15.61 | 106.63 ± 3.35 |
| N | 11 | 9 |
| Yac 0.01 + Black Maca | | |
| Mean ± standard error | 122.38 ± 12.14 | 107.75 ± 6.07 |
| N | 9 | 9 |
| Yac 0.1 + Black Maca | | |
| Mean ± standard error | 92.94 ± 19.34 | 108.43 ± 4.72 |
| N | 10 | 10 |
| Yac 1 + Black Maca | | |
| Mean ± standard error | 110.59 ± 28.28 | 97.82 ± 6.20 |
| N | 9 | 10 |
| Commercial Yac + Black Maca | | |
| Mean ± standard error | 123.93 ± 19.43 | 94.67 ± 4.81 |
| N | 5 | 5 |

The atomized black maca produces an increase in the total number of spermatozoids in the epididymis both after 3 days and after 7 days of treatment. These values are maintained with the yacon at the three studied doses. The commercial yacon did not alter either the effect of the black maca in the number of spermatozoids.

TABLE 3

Treatment with a mixture of black maca (BM) and yacon during 3 days

| GLUCOSE mg/dl | Control | MN | Yacon 0.01 + MN | Yacon 0.1 + MN | Yacon 1 + MN | CommYacon + MN |
|---|---|---|---|---|---|---|
| Mean | 136.23 | 113.50* | 114.23* | 111.69* | 110.46* | 114.00* |
| SD | 11.99 | 10.72 | 10.52 | 12.88 | 9.15 | 7.92 |
| SE | 3.20 | 2.86 | 2.81 | 3.44 | 2.45 | 2.12 |

*p < 0.001 as compared to the control. There are no differences between samples with yacon 0.01 (0.01 g/kg) and yacon (1 g/kg). CommYacon: Yacon obtained in a commercial store.

TABLE 4

Treatment with a mixture of black maca and yacon during 7 days

| GLUCOSE mg/dl | Control | BM | Yac 0.01 + MN | Yac 0.1 + MN | Yac 1 + MN | Yac Com + MN |
|---|---|---|---|---|---|---|
| Mean | 113.65 | 108.48 | 101.43** | 101.88** | 96.70* | 106.20 |
| SD | 12.38 | 7.63 | 11.39 | 9.52 | 4.90 | 2.81 |
| SE | 3.73 | 2.30 | 3.43 | 2.87 | 1.48 | 0.85 |

*p < 0.001;
***p < 0.05 as compared to the control

TABLE 5

Effect of different compositions of boiled aqueous extracts of red maca (RM) and yacon in the weight f the ventral prostate as well as in the glycemia values in rats treated with testosterone entantate (TE).

| Treatment | Ventral Prostate (g) mean ± standard | Glycemia (mg/dl) mean ± standard error |
|---|---|---|
| TE | 0.84 ± 0.03 | 120.50 ± 5.18 |
| TE + RM/Yacon 10/90 | 0.66 ± 0.05** | 99.40 ± 5.39** |
| TE + RM/yacon 50/50 | 0.63 ± 0.02** | 119.83 ± 3.59 |
| TE + RM/yacon 90/10 | 0.54 ± 0.03* | 90.00 ± 2.45* |
| Probability | *P < 0.01; **P < 0.05 regarding TE | *P < 0.01; **P < 0.05 regarding TE |

TABLE 6

Association between the levels of total polyphenols (mean and Standard error) and antioxidant activity in the black maca (BM).

| Samples | Polyphenols (g/100 g) | Antioxidant activity (%)* |
|---|---|---|
| BM in boiled 50% Ethanol | 0.45 (0.01) | 52.05 |
| BM in boiled 70% Ethanol | 0.44 (0.003) | 50.19 |
| BM in sonicated 50% ethanol | 0.38 (0.002) | 43.97 |
| BM in sonicated 70% ethanol | 0.36 (0.02) | 42.11 |
| BM macerated in hydroalcoholic solution | 0.06 (0.001) | 10.00 |

*A 0.25 mg/ml sample was used

REFERENCES

Alvarez F P P, Jurado T B, Calixto C M, Incio V N, Silva A J. [Prebiotic inulin/oligofructose in Yacon root (*Smallanthus sonchifolius*), phytochemistry and standardization as basis for clinical and pre-clinical research] [Article in Spanish]. Rev Gastroenterol Peru. 2008 January-March;28(1):22-7.

Amore M, Di Donato P, Berti A, Palareti A, Chirico C, Papalini A, Zucchini S. Sexual and psychological symptoms in the climacteric years. Maturitas. 2007 Mar. 20; 56(3):303-11.

AFSSA. Opinion: Of the French Agency of sanitary security of foods regarding the evaluation of the consumer's health risk of using the pulverized maca root, commercialized as such or in composition with food supplements. Afssa-Saisina N$^a$ 2004-SA-0155. 2004.

Aybar M J, Sánchez Riera A N, Grau A, Sánchez SS. Hypoglycemic effect of the water extract of *Smallantus sonchifolius* (yacon) leaves in normal and diabetic rats. J Ethnopharmacol. 2001 February; 74(2):125-32.

Canales M, Aguilar J, Prada A, Marcelo A, Huamán C, Carvajal L. Nutricional evaluation of *Lepidium meyenii* (Maca) in albino mice and their descendants [in Spanish]. Arch. Latinoamer. Nutr 2000; 50: 126-133.

Chacón G. Phytochemical studies of *Lepidium meyenii* Walp. Bachelor Thesis in Biology. Universidad Nacional Mayor de San Marcos. Lima:Peru. 1961.

Cieza de León. Crónicas del Perú. Primera Parte. 1553; 240: 354.

Cobo B. Historia del Nuevo Mundo. Biblioteca de Autores Españoles. 1653.Sevilla:España. 1956. 430 pp.

Cóndor Suriaqui, D A. Influence of maca in the weight increase in the reproduction and descendants of ewe hoggs in the community cooperative San Ignacio de Junín. Thesis to opt for the title of zootechnic engineer in the Universidad Nacional Daniel Alcides Carrión, Cerro de Pasco. 1991

Córdova H E. La maca raíz nutritive de los andes. Ministerio de Agricultura: Cerro de Pasco. 2003. 88 pp.

De Rivero and Ustariz M E. Memoria sobre algunos ramos de la agriculture del Perú. In: Colección de Memorias Científicas, Agrícolas e Industriales. Tome II. Imprenta de H. Goemare: Brussels. 1897: 218-228.

Dou D Q, Tian F, Qiu Y K, Kang T G, Dong F. Structure elucidation and complete NMR spectral assignments of four new diterpenoids from *Smallantus sonchifolius*. Magn Reson Chem. 2008 May 9. [Epub ahead of print]

Elsabagh S, Hartley D E, File S E. Limited cognitive benefits in Stage +2 postmenopausal women after 6 weeks of treatment with *Ginkgo biloba*.J Psychopharmacol. 2005:19: 173-81

Fahey J W, Zalcmann A T, Talalay P: The chemical diversity and distribution of glucosinolates and isothiocyanates among plants. Phytochemistry 2001, 56:5-51.

Gasco M, Aguilar J D, Gonzales G F. Effect of chronic treatment with three varieties of *Lepidium meyenii* (Maca) on reproductive parameters and DNA quantification in adult male rats. Andrologia. 2007;39:151-8.

Gasco M, Yucra S, Rubio J, Gonzales G F. *Lepidium meyenii* (Maca) varieties did not alter female reproductive parameters in adult male rats. Journal of Complementary and Integrative Medicine. 2008.

Genta S B, Cabrera W M, Grau A, Sánchez SS. Subchronic 4-month oral toxicity study of dried *Smallanthus sonchifolius* (yacon) roots as a diet supplement in rats. Food Chem Toxicol. 2005 November;43(11):1657-65.

Gonzales C, Rubio J, Gasco M, Nieto J, Yucra S, Gonzales G F. Effect of short-term and long-term treatments with three ecotypes of *Lepidium meyenii* (MACA) on spermatogenesis in rats. Journal of Ethnopharmacology. 2006; 103: 448-454.

Gonzales G F, Córdova A, Gonzales C, Chung A, Vega K, Villena A. Lepidium meyenii (Maca) increased semen parameters in adult men. Asian Journal of Andrology. 2001; 3: 301-303.

Gonzales G F, Ruiz A, Gonzales C, Villegas L, Córdova A. Effect of Lepidium meyenii (Maca) roots, a Peruvian plant on spermatogenesis of male rats. Asian Journal of Andrology. 2001; 3: 231-233.

Gonzales G F, Vásquez V, Rodríguez D, Maldonado C, Mormontoy J, Portella J, Pajuelo M, Villegas L, Gasco M. Effect of two different extracts of red maca in male rats with testosterone-induced prostatic hyperplasia. Asian Journal of Andrology 2007: Asian J Androl. 2007;9:245-251.

Gonzales G F, Miranda S, Nieto J, Fernandez G, Yucra S, Rubio J, Yi P, Gasco M. Red Maca (Lepidium meyenii) reduced prostate size in rats. Reproductive Biology and Endocrinology. 2005; 3(1):5

Gonzales G F (2006) Maca: From the Tradition to the Sciences. Lima, Peru. UPCH:Lima. 250 pp Gonzales G F. Biological effects of Lepidium meyenii, Maca, a plant from the highlands of Peru. In. Natural Products. Series: Recent Progress in Medicinal Plants. Ed. V. K. Singh, R. Bhardwaj, J N. Govil, RKr. Sharma. Studium Press LLC: USA. 2006a; 15: 217-242.

Gonzales G F, Vasquez V, Gasco M, Villegas L, Rubio J, Gonzales C. Procesamiento de la maca. In: Maca de la Tradición a la ciencia. Lima, Peru. UPCH:Lima. 2006a: 47-67.

Gonzales G F, Valerie L G Jr. Medicinal Plants from Peru: A review of plants as potential agents against cancer. Anti-Cancer Agents in Medicinal Chemistry. 2006; 6: 429-444.

Gonzáles G F, Gasco M, Malheiros-Pereira A, Gonzales-Castañeda C. Antagonistic effect of lepidium meyenii (red maca) on prostatic hyperplasia in adult mice. Andrologia. 2008;40: 179-185.

Hong SS, Lee S A, Han X H, Lee M H, Hwang J S, Park J S, Oh K W, Han K, Lee M K, Lee H, Kim W, Lee D, Hwang B Y. Melampolides from the leaves of Smallanthus sonchifolius and their inhibitory activity of lps-induced nitric oxide production. Chem Pharm Bull (Tokyo). 2008 February;56(2):199-202.

Johns T. The anu and the maca. J Ethnobiol 1981; 1:208-212.

Lee K-J, Dabrowski K, Rinchard J, Gomez C, Guz L, Vilchez C. Supplementation of maca (Lepidium meyenii) tuber meal in diets improves growth rate and survival of rainbow trout Oncorhynchus mykiss (Walbaum) alevins and juveniles. Aquac res 2004; 35: 215-223.

León J. The maca (Lepidium meyenii). A little known food plant of Peru. Economic Botany 1964; 18: 122-127.

Li G, Ammermann U, Quiros C F. Glucosinolate contents in maca (Lepidium peruvianum chacon) seeds, sprouts, mature plants and several derived commercial products. Economic Botany 2001; 55: 255-262.

Li J W, Liu J, Yang Y, Zheng MM, Rong T Z. [Improvement on microwave technology of extracting polysaccharide from yacon leaves] [Article in Chinese]. Zhong Yao Cai. 2007 November_; 30(11):1449-52.

Lin F, Hasegawa M, Kodama O. Purification and identification of antimicrobial sesquiterpene lactones from yacon (Smallanthus sonchifolius) leaves. Biosci Biotechnol Biochem. 2003 October; 67(10):2154-9.

Lobo A R, Colli C, Alvares E P, Filisetti T M. Effects of fructans-containing yacon (Smallanthus sonchifolius Poepp and Endl.) flour on caecum mucosal morphometry, calcium and magnesium balance, and bone calcium retention in growing rats. Br J Nutr. 2007 April;97(4):776-85.

Marin-Bravo M. Histología de la maca, Lepidium meyenii Walpers (Brassicaceae). Ver. Per. Biol 2003; ya:101-108.

Matos Mendieta R. La maca: una planta peruana en extinción. En Cielo Abierto, Cerro de Pasco, Centromin Peru. 1975: N° 5.

Matsuura T, Yoshikawa Y, Masui H, Sano M. [Suppression of glucose absorption by various health teas in rats] [Article in Japanese] Yakugaku Zasshi. 2004 April; 124(4) :217-23.

Matusheski N V, Juvik J A, Jeffery E H. Heating decreases epithiospecifier protein activity and increases sulforaphane formation in broccoli. Phytochemistry. 2004:65:1273-81

Narai-Kanayama A, Tokita N, Aso K. Dependence of fructooligosaccharide content on activity of fructooligosaccharide-metabolizing enzymes in yacon (Smallanthus sonchifolius) tuberous roots during storage. J Food Sci. 2007 August; 72(6):S381-7.

U.S. Pat. No. 6,267,995 (Lepidium meyenii root extracts for applications in pharmacy). 1999

Pedreschi R, Campos D, Noratto G, Chirinos R, Cisneros-Zevallos L. Andean yacon root (Smallanthus sonchifolius Poepp. Endl) fructooligosaccharides as a potential novel source of prebiotics. J Agric Food Chem. 2003 Aug. 27; 51(18):5278-84.

Quiroz C, Aliaga R. Maca (Lepidium meyenii Walp). Andean roots and tubers: ahipa, arracacha, maca and yacon. Promoting the conservation and use of underutilized neglected crops. 21.Hermann M and Hellers J. Editors. Internacional Plant Genetic Resources Institute, Rome, Italy. 1997: 173-197.

Rubio J, Caldas M, Dávila S, Gasco M, Gonzales G F. Effect of three different cultivars of Lepidium meyenii (Maca) on learning and depression in ovariectomized mice. BMC Complementary and Alternative Medicine 2006, 6:23.

Rubio J, Riqueros M I, Gasco M, Yucra S, Miranda S, Gonzales G F. Lepidium meyenii (Maca) reversed the lead acetate induced-Damage on reproductive function in male rats. Food Chem Toxicol. 2006a; 44:1114-1122

Rubio J, Dang H, Gong M, Liu X, Chen S-L, Gonzales G F. Aqueous and hydroalcoholic extracts of Black Maca (Lepidium meyenii) improve scopolamine-induced memory impairment in mice. Food and Chemical Toxicology. 2007; 45:1882-1890.

Ruiz H. Relación histórica del viaje a los reinos del Perú y Chile, 1777-1778, Madrid. Academia de Ciencias Exactas: Fis y Nat 1952: 526 pp.

Ruiz-Luna AC, Salazar S, Aspajo N J, Rubio J, Gasco M, Gonzales G F. Lepidium meyenii (Maca) increases litter size in normal adult female mice. Reproductive Biology and Endocrinology 2005; 3(1):1.

Sandoval M, Okuhama NN, Angeles F M, Melchor V V, Condezo L A, Lao J, Miller M J S. Antioxidant activity of the cruciferous vegetable Maca (Lepidium meyenii) Food Chemistry 2002; 79: 207-213.

Shen Y C, Chen S L, Wang C K. Contribution of tomato phenolics to antioxidation and down-regulation of blood lipids. J Agric Food Chem. 2007;55:6475-81.

Simonovska B, Vovk I, Andrensek S, Valentová K, Ulrichová J. Investigation of phenolic acids in yacon (Smallanthus sonchifolius) leaves and tubers. J Chromatogr A. 2003 Oct. 17; 1016(1):89-98.

Spitaler R, Winkler A, Lins I, Yanar S, Stuppner H, Zidorn C. Altitudinal variation of phenolic contents in flowering heads of Arnica montana cv. ARBO: a 3-year comparison. J Chem Ecol. 2008;34:369-75.

Stintzing F C, Hoffmann M, Carle R. Thermal degradation kinetics of isoflavone aglycones from soy and red clover Mol Nutr Food Res. 2006;50(4-5):373-7.

Takenaka M, Yan X, Ono H, Yoshida M, Nagata T, Nakanishi T. Caffeic acid derivatives in the roots of yacon (*Smallanthus sonchifolius*). J Agric Food Chem. 2003 Jan. 29; 51 (3) :793-6.

Tapia A, López C, Marcelo A, Aguilar J L. The maca (*Lepidium meyenii*) and their effect anti-stress in an animal model in mice [in Spanish]. Acta Andina 1999-2000; 8: 45-56.

Tello J, Hermann M, Calderón A. La maca (*Lepidium meyenii* Walp) cultivo alimenticio potencial para las zonas andinas. Boletín de Lima 1992; 14: 59-66.

Tello R y Porras M. "Estudio técnico para la elaboración de licor de maca (*Lepidium meyenii* Walp) por maceración" Research work carried out at the Universidad Nacional del Centro del Perú. 1999.

Terada S, Ito K, Yoshimura A, Noguchi N, Ishida T. [Constituents relating to anti-oxidative and alpha-glucosidase inhibitory activities in Yacon aerial part extract] [Article in Japanese] Yakugaku Zasshi. 2006 August; 126(8) :665-9.

Valentová K, Stejskal D, Bartek J, Dvoráčková S, Kren V, Ulrichová J, Simánek V. Maca (*Lepidium meyenii*) and yacon (*Smallanthus sonchifolius*) in combination with silymarin as food supplements: in vivo safety assessment. Food Chem Toxicol. 2008 March;46(3):1006-13.Epub 2007 Nov. 1.

Valentová K, Truong N T, Moncion A, de Waziers I, Ulrichová J. Induction of glucokinase mRNA by dietary phenolic compounds in rat liver cells in vitro. J Agric Food Chem. 2007 Sep. 19;55(19):7726-31.Epub 2007 Aug. 23.

Valentová K, Lebeda A, Dolezalová I, Jirovský D, Simonovska B, Vovk I, Kosina P, Gasmanová N, Dziechciarková M, Ulrichová J. The biological and chemical variability of yacon. J Agric Food Chem. 2006 Feb. 22; 54(4):1347-52.

Valentová K, Moncion A, de Waziers I, Ulrichová J. The effect of *Smallanthus sonchifolius* leaf extracts on rat hepatic metabolism. Cell Biol Toxicol. 2004 March; 20(2): 109-20.

Valentová K, Sersen F, Ulrichová J. Radical scavenging and anti-lipoperoxidative activities of *Smallanthus sonchifolius* leaf extracts. J Agric Food Chem. 2005 Jul. 13; 53(14): 5577-82.

Valentová K, Ulrichová J. *Smallanthus sonchifolius* and *Lepidium meyenii* —prospective Andean crops for the prevention of chronic diseases. Biomed Pap Med Fac Univ Palacky Olomouc Czech Repub. 2003 December;147(2): 119-30.

Valentova K, Cvak L, Muck A, Ulrichova J, Simanek V. Antioxidant activity of extracts from the leaves of *Smallanthus sonchifolius*.Eur J Nutr. 2003 January;42(1):61-6.

Valerio L, Gonzales G F. Toxicological Aspects of South American Herbs: Uncaria tomentosa (Cat's Claw) and *Lepidium meyenii* (Maca). A Critical Synopsis. Toxicological Reviews 2005; 24: 11-35.

Yan X, Suzuki M, Ohnishi-Kameyama M, Sada Y, Nakanishi T, Nagata T. Extraction and identification of antioxidants in the roots of yacon (*Smallanthus sonchifolius*). J Agric Food Chem. 1999 November; 47(11):4711-3.

Yllescas Ma G (1994) Estudio químico y Fitoquímico comparative de tres ecotipos de *Lepidium meyenii* Walp "maca" procedente de Carhuamayo (Junín). Professional Aptitude Work to opt for the Title of Chemical Pharmacist. Univ. Nac Mayor de San Marcos. Lima, Perú.

Yoshida M, Ono H, Mori Y, Chuda Y, Mori M. Oxygenation of bisphenol A to quinones by polyphenol oxidase in vegetables. J Agric Food Chem. 2002 Jul. 17;50(15):4377-81.

Yucra S, Gasco M, Rubio J, Nieto J, Gonzales G F. Effect of different fractions from hydroalcoholic extract of Black Maca (*Lepidium meyenii*) on testicular function in adult male rats. Fertil Steril. 2007 Jul. 30; [Epub ahead of print]

Zheng B L, He K, Kim C H, Rogers L, Yu S, Huang Z Y, Lu Y, Yan S J, Qien L C, Zhen Q Y. Effect of a lipidic extract from *Lepidium meyenii* on sexual behavior in mice and rats. Urology 2000; 55: 598-602.

Zolezzi 0.Transformación de la uña de gate y la maca en el Perú. In: Third encounter of the rural agribusiness. Tarapoto, Peru. 1997.

Having described the present inventions, it is considered a novelty and, therefore, the property is claimed of that contained in the following claims:

1. A composition comprising 3 grams of atomized or lyophilized *Lepidium meyenii* hypocotyls extract and 1 gram of atomized or lyophilized *Smallanthus sanchifolius* extract.

2. The composition according to claim 1, wherein the *Lepidium meyenii* extract is a boiled aqueous extract of red *Lepidium meyenii* and the *Smallanthus sanchifolius* extract is a *Smallanthus sanchifolius* roots extract.

3. The composition according to claim 1, wherein the *Lepidium meyenii* extract is a boiled aqueous extract of red *Lepidium meyenii* and the *Smallanthus sanchifolius* extract is a *Smallanthus sanchifolius* leaves extract.

4. The composition according to claim 1, wherein the *Lepidium meyenii* extract is a boiled 50% hydroalcoholic extract of red *Lepidium meyenii* and the *Smallanthus sanchifolius* extract is a *Smallanthus sanchifolius* roots extract.

5. The composition according to claim 1, wherein the *Lepidium meyenii* extract is a boiled 50% hydroalcoholic extract of red *Lepidium meyenii* and the *Smallanthus sanchifolius* extract is a *Smallanthus sanchifolius* leaves extract.

6. The composition according to claim 1, wherein the *Lepidium meyenii* extract is a boiled 70% hydroalcoholic extract of red *Lepidium meyenii* and the *Smallanthus sanchifolius* extract is a *Smallanthus sanchifolius* roots extract.

7. The composition according to claim 1, wherein the *Lepidium meyenii* extract is a boiled 70% hydroalcoholic extract of red *Lepidium meyenii* and the *Smallanthus sanchifolius* extract is a *Smallanthus sanchifolius* leaves extract.

8. The composition according to claim 1, wherein the *Lepidium meyenii* extract is a boiled aqueous extract of black *Lepidium meyenii* and the *Smallanthus sanchifolius* extract is a *Smallanthus sanchifolius* roots extract.

9. The composition according to claim 1, wherein the *Lepidium Meyenii* extract is a boiled aqueous extract of black *Lepidium meyenii* and the *Smallanthus sanchifolius* extract is a *Smallanthus sanchifolius* leaves extract.

10. The composition according to claim 1, wherein the *Lepidium meyenii* extract is a boiled 50% hydroalcoholic extract of black *Lepidium meyenii* and the *Smallanthus sanchifolius* extract is a *Smallanthus sanchifolius* roots extract.

11. The composition according to claim 1, wherein the *Lepidium meyenii* extract is a boiled 50% hydroalcoholic extract of black *Lepidium meyenii* and the *Smallanthus sanchifolius* extract is a *Smallanthus sanchifolius* leaves extract.

12. The composition according to claim 1, wherein the *Lepidium meyenii* extract is a boiled 70% hydroalcoholic extract of black *Lepidium meyenii* and the *Smallanthus sanchifolius* extract is a *Smallanthus sanchifolius* roots extract.

13. The composition according to claim 1, wherein the *Lepidium meyenii* extract is a boiled 70% hydroalcoholic extract of black *Lepidium meyenii* and the *Smallanthus sanchifolius* extract is a *Smallanthus sanchifolius* leaves extract.

14. The composition according to claim 1, wherein the *Lepidium meyenii* extract is a red *Lepidium meyenii* extract macerated in 50% hydroalcoholic solution and the *Smallanthus sanchifolius* extract is a *Smallanthus sanchifolius* roots extract.

15. The composition according to claim 1, wherein the *Lepidium meyenii* extract is a red *Lepidium meyenii* extract macerated in 50% hydroalcoholic solution and the *Smallanthus sanchifolius* extract is a *Smallanthus sanchifolius* leaves extract.

16. The composition according to claim 1, wherein the *Lepidium meyenii* extract is a red *Lepidium meyenii* extract macerated in 70% hydroalcoholic solution and the *Smallanthus sanchifolius* extract is a *Smallanthus sanchifolius* roots extract.

17. The composition according to claim 1, wherein the *Lepidium meyenii* extract is a red *Lepidium meyenii* extract macerated in 70% hydroalcoholic solution and the *Smallanthus sanchifolius* extract is a *Smallanthus sanchifolius* leaves extract.

18. The composition according to claim 1, wherein the *Lepidium meyenii* extract is a black *Lepidium meyenii* extract macerated in 50% hydroalcoholic solution and the *Smallanthus sanchifolius* extract is a *Smallanthus sanchifolius* roots extract.

19. The composition according to claim 1, wherein the *Lepidium meyenii* extract is a black *Lepidium meyenii* extract macerated in 50% hydroalcoholic solution and the *Smallanthus sanchifolius* extract is a *Smallanthus sanchifolius* leaves extract.

20. The composition according to claim 1, wherein the *Lepidium meyenii* extract is a black *Lepidium meyenii* extract macerated in 70% hydroalcoholic solution and the *Smallanthus sanchifolius* extract is a *Smallanthus sanchifolius* roots extract.

21. The composition according to claim 1, wherein the *Lepidium meyenii* extract is a black *Lepidium meyenii* extract macerated in 70% hydroalcoholic solution and the *Smallanthus sanchifolius* extract is a *Smallanthus sanchifolius* leaves extract.

* * * * *